United States Patent [19]

Breuer et al.

[11] 4,049,651

[45] Sept. 20, 1977

[54] ALKOXY AND ALKYLTHIOALKYLUREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[21] Appl. No.: 678,001

[22] Filed: Apr. 19, 1976

[51] Int. Cl.² .......................................... C07D 501/36
[52] U.S. Cl. ............................... 544/21; 424/246; 544/23; 544/26; 544/27
[58] Field of Search ................ 160/243 C; 260/243 C

[56] References Cited

U.S. PATENT DOCUMENTS

| 3,708,479 | 1/1973 | Welch et al. | 260/243 C |
| 3,925,368 | 12/1975 | Cooper et al. | 260/243 C |
| 3,948,904 | 4/1976 | Patchornik et al. | 260/243 C |

*Primary Examiner*—Nicholas S. Rizzo
*Assistant Examiner*—David E. Wheeler
*Attorney, Agent, or Firm*—Lawrence S. Levinson; Merle J. Smith; Stephen B. Davis

[57] ABSTRACT

Alkoxy and alkylthioalkylureido cephalosporins of the formula

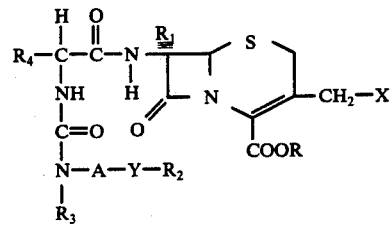

wherein R is hydrogen, lower alkyl, phenyl-lower alkyl, diphenyl-lower alkyl, tri(lower alkyl)silyl, trihaloethyl, a salt forming ion, or the group

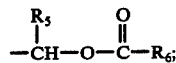

$R_1$ is hydrogen or methoxy; A is straight or branched chain alkylene of 1 to 6 carbons; $R_2$ is lower alkyl; Y is O or S; $R_3$ is hydrogen or lower alkyl; $R_4$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_5$ is hydrogen or lower alkyl; $R_6$ is lower alkyl; and X is hydrogen, lower alkanoyloxy,

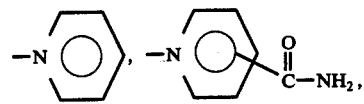

or certain heterothio groups; are disclosed. These compounds are useful as antibacterial agents.

18 Claims, No Drawings

ALKOXY AND ALKYLTHIOALKYLUREIDO CEPHALOSPORINS

BACKGROUND OF THE INVENTION

Cephalosporins having a ureido acyl side chain are disclosed in U.S. Pat. No. 3,673,183; 3,708,479; 3,833,568; and 3,860,591. Cephalosporins having various acyl side chains and a 7α-methoxy substituent are taught in various patents including U.S. Pat. Nos. 3,775,410; 3,780,031; 3,780,033; 3,780,034; 3,780,037; 3,843,641; etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to a new alkoxy and alkylthioalkylureido-7α-methoxy or desmethoxy cephalosporin derivatives of the formula

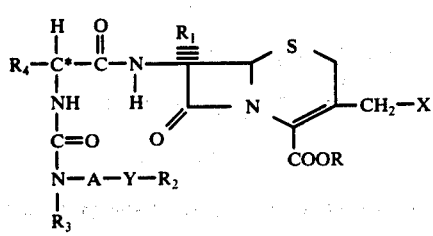

(I)

R represents hydrogen, lower alkyl, phenyl-lower alkyl, diphenyl-lower alkyl, tri(lower alkyl)silyl, trihaloethyl, a salt forming ion, or the group

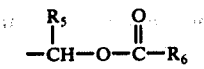

wherein $R_5$ is a hydrogen or lower alkyl and $R_6$ is lower alkyl.

$R_1$ represents hydrogen or methoxy. The $R_1$ substituent is in the α-configuration as indicated by the broken lines (≡).

A represents straight or branched chain alkylene of 1 to 6 carbons.

$R_2$ represents lower alkyl.

Y represents O or S.

$R_3$ represents hydrogen or lower alkyl.

$R_4$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

X represents hydrogen, lower alkanoyloxy, certain heterothio groups

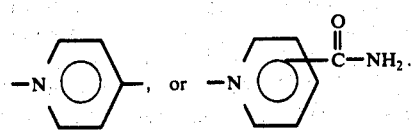

When X is pyridinium or carbamoyl substituted pyridinium, the compounds can be structurally represented as having the formula (Ia)

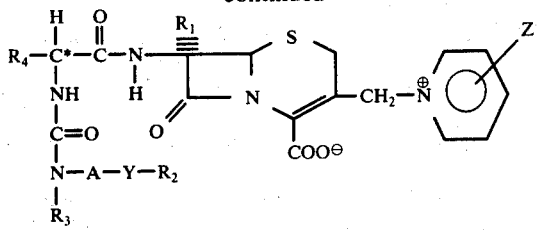

wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, preferably benzyl, phenethyl, and diphenylmethyl.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or more substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

Straight or branch chain alkylene of 1 to 6 carbons is intended to include groups such as $-(CH_2)_n-$ wherein $n$ is an integer from 1 to 6,

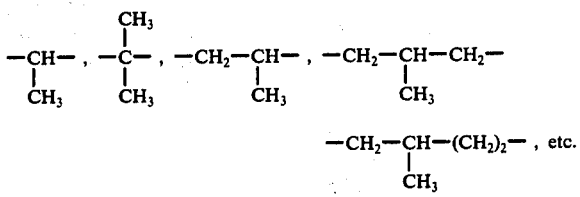

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R,2,2,2-trichloroethyl is preferred.

Trimethylsilyl is the preferred tri(lower alkyl)silyl group.

The heterocyclic groups represented by $R_4$ are 2-thienyl, 3-thienyl, 2-furyl, 3-furyl, 2-pyridyl, 3-pyridyl, or 4-pyridyl. Also included within the meaning of $R_4$ are such heterocyclics having a halogen (preferably Cl or Br) or a lower alkyl of 1 to 4 carbons (preferably methyl or ethyl) substituent, i.e. 2-(4-chlorothienyl), 3-(4-methylthienyl), etc.

Lower alkanoyloxy refers to a group of the formula

lower alkyl wherein lower alkyl is of 1 to 4 carbons, preferably wherein lower alkyl is methyl.

The heterothio groups represented by X are

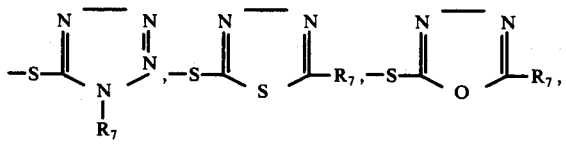

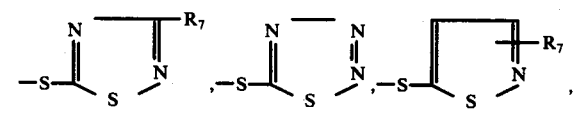

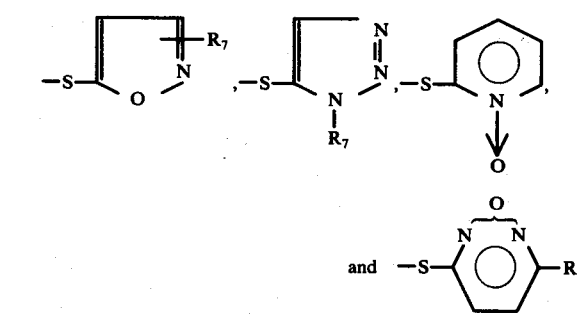

wherein $R_7$ is hydrogen or lower alkyl of 1 to 4 carbons (preferably methyl or ethyl) and $R_8$ is hydrogen, lower alkyl of 1 to 4 carbons (preferably methyl or ethyl), methoxy, hydroxy, or halogen (preferably chlorine).

The compounds of formula I wherein X is hydrogen, lower alkanoyloxy, or heterothio and $R_2$ is lower alkyl are prepared by reacting an α-amino intermediate of the formula

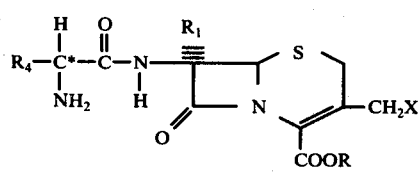

wherein X is hydrogen, lower alkanoyloxy, or heterothio, preferably in the form of its trifluoroacetic acid salt, with a compound of the formula $$R_2-Y-A-N=C=O \qquad (III)$$

or

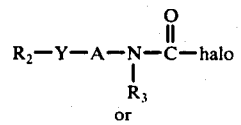

or

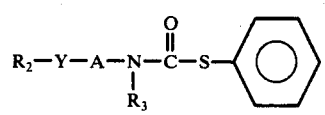

wherein $R_2$ is lower alky; Y is O or S; $R_3$ is hydrogen or lower alkyl; A is as defined above; and halo is Cl or Br.

The intermediates of the formulas II to V are prepared by known methods. For example, the compounds of formula II can be prepared by various methods including the acylation of a 7-amino cephalosporin of the formula

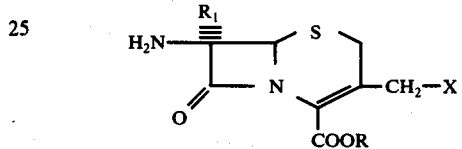

with a substituted α-amino acid of the formula

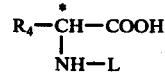

wherein L is a protecting group such as

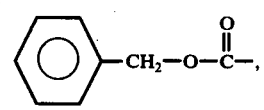

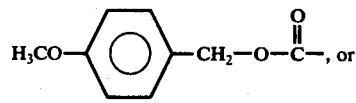

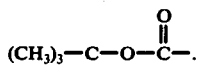

The α-amino protecting group is then removed by treating the resulting cephalosporin with trifluoroacetic acid and anisole. The desmethoxy α-amino compounds of formula II are taught in various patents as for example, U.S. Pat. Nos. 3,485,819; 3,507,861; 3,641,021; 3,796,801; 3,813,388; 3,821,207; etc. Similarly, the 7α-methoxy compounds of formula II prepared by various means are disclosed in patents as for example U.S. Pat. Nos. 3,775,410; 3,780,031; 3,780,033; 3,780,034; 3,780,037; 3,887,549; etc. Also, the 7α-methoxy-7-amino compounds of formula VI are taught in U.S. Pat. No. 3,897,424.

The compounds of formula III wherein Y is O are disclosed, for example, by Zenner et al., Chem. Abst. Vol. 64, 19413g (1966), and those wherein Y is S are disclosed, for example, by Boehme et al., Chem. Abst., Vol. 71, 3847m (1969). Various compounds of formula IV are disclosed by Koenig et al., Chem. Abst., Vol. 64, 1972h (1966), etc.

The compound of formula I wherein $R_1$ is either hydrogen or methoxy and X is pyridinium or carbamoyl substituted pyridinium are prepared by reacting the compound of th formula (or its sodium salt)

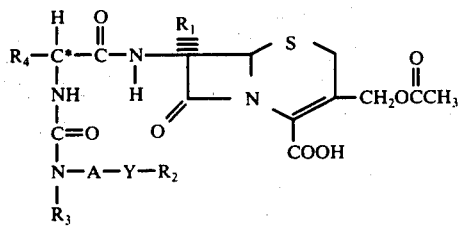
(Ib)

with pyridine or carbamoyl substituted pyridine in a polar solvent such as water and in the presence of a catalyst such as an alkali metal thiocyanate. U.S. Pat. No. 3,792,047 and German Offenlegungsschrift 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ib with a mercaptan of the formula

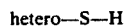
(VIII)

or an alkali metal (preferably sodium) mercaptan salt of the formula

(IX)

Methods for displacing the acetoxy group of a cephalosporin by a heterothio group are taught in various patents including U.S. Pat. Nos. 3,855,213; 3,890,309; 3,892,737; etc.

Alternatively, the compounds of formula I wherein X is hydrogen, lower alkanoyloxy, or heterothio can be prepared by reacting a compound of the formula

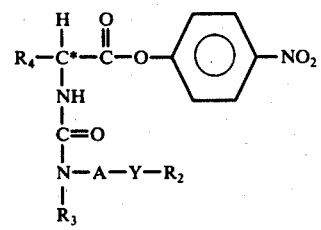
(X)

wherein $R_2$, $R_3$, $R_4$, A, and Y are as defined above with an ester, preferably R is diphenylmethyl, of the compound of formula VI.

The compound of formula X can be prepared by reacting the isocyanatoacetic acid ester of the formula

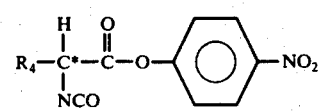
(XI)

with an amine of the formula (XII)

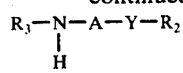

The compounds of formula I wherein R is lower alkyl, phenyl-lower alkyl, trihaloethyl, diphenyl-lower alkyl, or the acyloxymethyl group

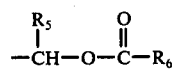

may be obtained by reacting the 7-amino cephalosporin of formula VI either before or after the acylation of the 7-amino substituent with one or two moles of a compound of the formula halo—R—(XII)

or

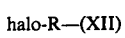
(XIV)

wherein halo is preferably chlorine or bromine in an inert solvent such as dimethylformamide, acetone, dioxane, benezne, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e. R is hydrogen, with any of the salt forming ions described above.

It will be appreciated that the compounds of formula I are optically active due to the presence of an asymmetric carbon atom represented as C* in the preceding formulas. By selection of the appropriate starting material it is possible to obtain the compoounds of formula I as a mixture of optically active isomers or isolated as a single isomer. The various isomers as well as their mixtures are within the scope of this invention. Also, a second asymmetric carbon atom can be present in the alkylene chain, for example

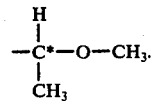

Preferred compounds of this invention are those wherein R is hydrogen or an alkali metal ion; X is pyridinium, carbamoyl substituted pyridinium (particularly where the carbamoyl group is in the 4-position), or heterothio; $R_4$ is cyclohexenyl, cyclohexadienyl, phenyl, benzyl, phenethyl, substituted phenyl, benzyl, or phenethyl wherein the substituent is on the phenyl ring and is one or two members selected from chloro, bromo, methyl, ethyl, methoxy, ethoxy and hydroxy, or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl, or ethyl; $R_2$ is straight or branched chain alkyl of 1 to 4 carbons; A is straight or branched chain alkylene of 1 to 4 carbons; and $R_3$ is hydrogen or straight or branched chain alkyl of 1 to 4 carbons.

Also preferred as both final products and intermediates are the compounds of formula I wherein X is

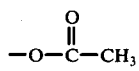

and A, R, $R_2$, $R_3$ and $R_4$ are as defined above.

The most preferred final compounds are those of formula I wherein R is hydrogen or an alkali metal ion; $R_4$ is 2-thienyl, 3-thienyl, phenyl, or 4-hydroxyphenyl; $R_2$ is straight or branched chain alkyl of 1 to 4 carbons; A is straight or branched chain alkylene of 1 to 4 carbons; $R_3$ is hydrogen; and X is heterothio, particularly wherein X is

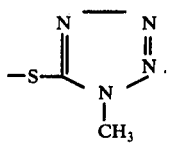

The compounds of formula I wherein R is hydrogen have a broad spectrum of antibacterial activity against both gram positive and gram negative organisms such as *Staphylococcus aureus, Salmonella schottmuelleri, Proteus rettgeri, Escherichia coli, Enterobacter hafniae, Enterobacter cloacae, Klebsiella pneumoniae*, etc. They may be used as antibacterial agents in a propylactic manner, e.g., in cleaning or as surface disinfecting compositions, or otherwise to combat infections due to organisms such as those named, above, and in general may be utilized in a manner similar to cephalothin and other cephalosporins. For example, a compound of formula I or a physiologically acceptable salt thereof may be used in various animal species in an amount of about 1 to 100 mg./kg. of body weight, daily, orally or parenterally, in single or two to four divided doses to treat infections of bacterial origin, e.g., 5.0 mg./kg. in mice.

Up to about 600 mg. of a compound of formula I wherein R is hydrogen or a physiologically acceptable salt thereof may be incorporated in an oral dosage form such as tablets, capsules or elixirs or in an injectable form in a sterile aqueous vehicle prepared according to conventional pharmaceutical practice.

They may also be used in cleaning or disinfecting compositions, e.g., for cleaning barns or dairy equipment, at a concentration of about 0.2 to 2% by weight of such compounds admixed with, suspended or dissolved in conventional inert dry or aqueous carriers for application by washing or spraying.

They are also useful as nutritional supplements in animal feeds.

Illustrative process details are provided in the examples for the various reactions. All temperatures are on the centigrade scale.

EXAMPLE 1

7β-[[D-[[[(Methoxymethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid a. D-2-[[[(4-Methoxyphenyl)methoxy]carbonyl]amino]-2-thiopheneacetic acid 74 g. of D-2-Thienylgylcine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°-94°; $[\alpha]_{20}^D$: −69° (c=1, tetrahydrofuran).

b. 7β-Amino-3-[[(1-methyl-1H-tetrazol-5-yl)thio]methyl]-8-oxo-5-thia-1-azabicyclo[4.2.0]oct-2-ene-2-carboxylic acid To a stirred suspension of 27.2 g. 7-amino cephalosporanic acid (0.1 mole) in 150 ml. of acetone and 100 ml. of $H_2O$ at 0−5° is added 50 ml. of 2N NaOH, with care being taken to keep the pH below 8.5. A solution of 12.7 g. (0.11 mole) of 1-methyl-5-mercapto-1H-tetrazole in 50 ml. of 2N NaOH is added, and the mixture is allowed to warn to room temperature. The stirred mixture is then maintained at 60° (internal temperature) under nitrogen for 3 hours at pH 7-7.5 by the periodic addition of dilute aqueous NaOH. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

c. 7β-Amino-3-[[(1-methyl-1H-tetrazol-5-yl)thio]methyl]-8-oxo-5-thia-1-azabicyclo[4.2.0]oct-2-ene-2carboxylic acid, diiphenylmethyl ester A mixture of 16.4 g. (0.05 mole) of the acid product from part (b), 10.3 g. (0.054 mole) p-toluenesulfonic acid monohydrate, 350 ml. of dioxane (dried by passage through basic alumina), and dry $CH_3OH$ in stirred at room temperature under nitrogen for 30 minutes. The clear solution is evaporated to a residue, and $H_2O$ and $CH_3OH$ are removed by four evaporations of 100 ml. quantities of dioxane. Fresh dioxane (300 ml.) is then added to the residue followed by a solution of crystalline diphenyldiazomethane (19.4 g., 0.10 mole) in 150 ml. of dry dimethoxyethane. The mixture is initially shaken vigorously for 10-15 minutes and then stirred at room temperature for 3 hours. Methanol (25 ml.) is added, and the red solution is stirred until it has turned yellow-orange. The solvents are removed in vacuo, and the residue is treated with 400 ml. of $CH_2Cl_2$ and a solution of 20 g. of $K_2HPO_4$ in 250 ml. of $H_2O$. The $CH_2Cl_2$ layer is washed with water and saturated NaCl, and finally dried (MgSO$_4$) to give a residue after removal of the solvent in vacuo. Treatment of the residue with $Et_2O$ gives a solid (27 g.). Column chromatography of this solid on silica gel by elution with $CHCl_3$ and then EtOAc-$CHCl_3$ (4:1) provides the desired product as a residue (12.9 g.). Treatment with EtOAc then provides 8.0 g. of the desired product as a pale yellow powder.

d. 7β-[[D-[[[(4-Methoxyphenyl)methoxy]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 46.2 g. of 7β-amino-3-[[(1-methyl-1H-tetrazol-5-yl)-thio]methyl]-8-oxo-5-thia-1-azabicyclo[4.2.0]oct-2-ene-2-carboxylic acid, diphenylmethyl ester from part (c) are dissolved in 550 ml. of anhydrous methylene chloride. 550 ml. of tetrahydrofuran and 36 g. of D-2-[[[(4-methoxyphenyl)-methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treatd with activated carbon, filtered and the filtrate is then concentrated slowly under vacuum to a small volume. After standing overnight in the refrigerator, the precipitate crystals are filtered under suction to obtain 63.1 g. of 7β-[[D-[[[(4-methoxyphenyl)methoxy]carbonyl]-amino]-2-thienylacetyl]amino]-3-[[(1-methyl-1H-tetrazol-5-yl)thio]methyl]-8-oxo-5-thia-1-azabicyclo[4.2.0-]oct-2-ene-2-carboxylic acid, diphenylmethyl ester; m.p. 130°-131° (dec.). $[\alpha]_{20}^D$: −117° (c=1, tetrahydrofuran).

e. 7β-[D-2-Amino-2-(thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1)

62 g. of the diphenylmethyl ester product from part (d) are addd to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg. and 35° bath temperature. The residue is treated with 250 ml. of petroleum ether, then 350 ml. of ether, stirred for one hour, and filtered with suction to yield 46.4 g. of 7β-[D-2-amino-2-(2-thienyl)acetamido]-3-[[(1-methyl-1H-tetrazol-5-yl)thio]-methyl]-8-oxo-5-thia-1-azabicyclo[4.2.0]oct-2-ene-2-carboxylic acid, trifluoroacetic acid salt (1:1); m.p. 138°-139° (dec.).

f. 7β-[[D-[[[(Methoxymethyl)amino]carbonyl]-amino]-2-thienylacetyl]amino]-3-[[(1-methyl-1H-tetrazol-5-yl)thio]methyl]-8-oxo-5-thia-1-azabicyclo[4.2.0-]oct-2-ene-2-carboxylic acid, triethylamine salt 1.16 g. of the trifluoroacetic acid salt product from part (e) are suspended in 25 ml. of methylene chloride and 0.53 ml. of triethylamine are added. The almost clear solution is cooled to 0°-5° and a solution of 0.26 g. of isocyanic acid, methoxymethyl ester in approximately 10 ml. of methylene chloride is added dropwise. This reaction solution is stirred for one hour at 0°-5° and one hour at room temperature. After concentrating and trituration with ether, 1.45 g. are obtained of 7β[[ D-[[[(methoxymethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, triethylamine salt; m.p. 56°-66° (dec.).

g. 7β-[[D-[[[(Methoxymethyl)amino]carbonyl]-amino]-2-thienyl-acetyl]amino]-3-[[(1-methyl-1H-tetrazol-5-yl)thio]methyl]-8-oxo-5-thia-1-azabicyclo[4.2.0]oct-2-ene-2-carboxylic acid 1.53 g. of the triethylamine salt from part (f) are dissolved in 20 ml. water and the solution is filtered and acidified to yield 0.58 g. of 7β-[[D-[[[(methoxymethyl)amino]-carbonyl]amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid; m.p. 171°-176° (dec.).

An aqueous equimolar solution of this acid and sodium bicarbonate is lyophilized to yield 7β-[[D-[[[(methoxymethyl)amino]carbonyl]amino]-2-thienylacetyl]-amino]-3-[[(1-methyl-1H-tetrazol-5-yl)thio]methyl]-8-oxo-5-thia-1-azabicyclo-[4.2.0]oct-2-ene-2-carboxylic acid, sodium salt; m.p. 206°-210° (dec.). In an analogous manner, by substituting potassium bicarbonate for the sodium bicarbonate one obtains the corresponding potassium salt.

Similarly, by following the above procedure but substituting L-2-thienylglycine for the D-isomer in part (a), one obtains 7β-[[L-[[[(methoxymethyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid and its sodium and potassium salts.

EXAMPLE 2

7β-[[D-[[[(Methylthiomethyl)amino]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid Following the procedure of example 1, but substituting an equivalent amount of isocyanic acid, methylthiomethyl ester for the methoxymethyl ester in part (f) one obtains 7β-[[D-[[[(methylthiomethyl)amino]carbonyl]amino-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, triethylamine salt. This triethylamine salt can then be converted to the free acid and eventually the sodium or potassium salt as taught in example 1(g).

Similarly, by following the procedure of this example an also employing L-2-thienylglycine in place of the D-2-thienylglycine, one obtains 7β-[[L-[[[(methylthiomethyl)-amino]carbonyl]amino]-2-thienylacetyl]-amino]-3-[[(1-methyl-1H-tetrazol-5-yl)thio]methyl]-8-oxo-5-thia-1-azabicyclo-[4.2.0]oct-2-ene-2-carboxylic acid and its sodium and potassium salt.

EXAMPLES 3-30

Following the procedure of examples 1 and 2 but employing the acylating agent shown in Col. I and the 7β-amino-7α-methoxy or desmethoxy-cephalosporanic acid ester shown in Col. II, one obtains the protected ester shown in Col. III. The protecting group and ester group are removed as the compound of Col. III is converted to its trifluoroacetic acid salt shown in Col. IV. The trifluoroacetic acid salt is reacted with the isocyanato compound of Col. V to yield the cephalosporanic acid compound shown in Col. VI. The compound of Col. VI can be reacted so as to reintroduce the ester group and yield the compound of Col. VII or can be treated according to known procedures to yield the corresponding salt.

| Col. I | Col. II |
| --- | --- |

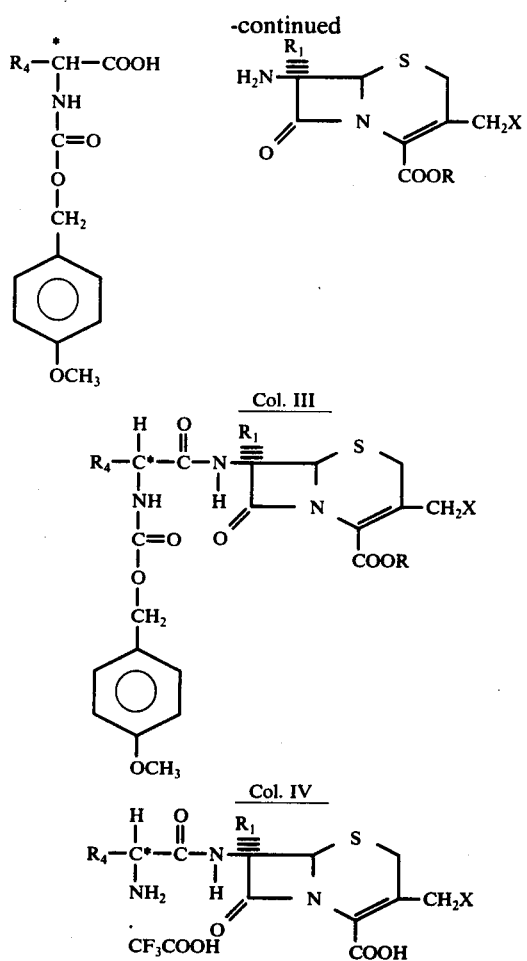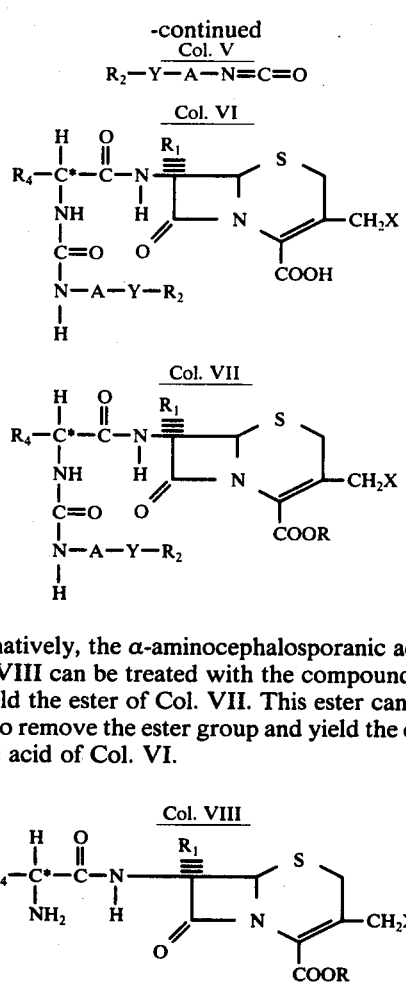

Alternatively, the α-aminocephalosporanic acid ester of Col. VIII can be treated with the compound of Col. V to yield the ester of Col. VII. This ester can then be treated to remove the ester group and yield the cephalosporanic acid of Col. VI.

| Ex. | $R_4$ | $A-Y-R_2$ | $R_1$ | R | X |
|---|---|---|---|---|---|
| 3 | thienyl | $-(CH_2)_2-O-CH_3$ | $-H$ | $-CH_2$-phenyl | $-S$-(1-methyltetrazol-5-yl) |
| 4 | 5-chlorothienyl | $-CH(CH_3)-S-C_2H_5$ | $-OCH_3$ | $-CH$(phenyl)$_2$ | $-S$-(1-methyltetrazol-5-yl) |
| 5 | 4-methylthienyl | $-(CH_2)_4-O-C_3H_7$ | $-H$ | $t-C_4H_9$ | $-S$-(5-methyl-1,3,4-thiadiazol-2-yl) |
| 6 | thienyl | $-CH_2-S-CH_3$ | $-H$ | $-CH$(phenyl)$_2$ | $-O-C(O)-C_2H_5$ |
| 7 | furyl | $-CH_2-O-C(CH_3)_3$ | $-H$ | $-C_2H_5$ | $-O-C(O)-CH_3$ |

-continued

| Ex. | R₄ | A—Y—R₂ | R₁ | R | X |
|---|---|---|---|---|---|
| 8 | furan (2-yl) | —CH(CH₃)—CH₂—S—C₅H₁₁ | —OCH₃ | —CH₂—C₆H₅ | —S-(1-ethyl-tetrazol-5-yl) |
| 9 | 5-chloro-furan-2-yl | —(CH₂)₆—O—CH₃ | —H | —CH(C₆H₅)₂ | —S-(5-methyl-1,3,4-thiadiazol-2-yl) |
| 10 | pyridin-2-yl | —CH₂—CH(CH₃)—CH₂—S—CH₃ | —OCH₃ | t-C₄H₉ | —S-(1H-1,2,3-triazol-5-yl) |
| 11 | 2-chloro-pyridin-4-yl | —CH₂—O—CH(CH₃)₂ | —H | —CH₂—C₆H₅ | —S-(5-methyl-1,3,4-oxadiazol-2-yl) |
| 12 | C₆H₅— | —CH₂—O—CH₃ | —H | —CH₂—C₆H₅ | —S-(4-methyl-thiazol-2-yl) |
| 13 | C₆H₅— | —(CH₂)₂—S—C₂H₅ | —OCH₃ | —CH(C₆H₅)₂ | —S-(1,3,4-thiadiazol-2-yl) |
| 14 | C₆H₅— | —C(CH₃)₂—CH₂—O—CH₃ | —H | —CH₂—C₆H₅ | —O—C(=O)—CH₃ |
| 15 | 4-HO—C₆H₄— | —CH(CH₃)—S—CH₃ | —OCH₃ | —CH(C₆H₅)₂ | —O—C(=O)—CH₃ |
| 16 | C₆H₅— | —CH(CH₃)—O—CH₃ | —H | —CH(C₆H₅)₂ | —S-(1-methyl-tetrazol-5-yl) |
| 17 | C₆H₅—CH₂— | —CH₂—S—C₄H₉ | —OCH₃ | —CH(C₆H₅)₂ | —S-(1-methyl-tetrazol-5-yl) |
| 18 | 4-HO—C₆H₄— | —(CH₂)₃—O—C₂H₅ | —H | —CH(C₆H₅)₂ | —S-(1-methyl-tetrazol-5-yl) |
| 19 | 3,5-dichloro-C₆H₃— | —(CH₂)₅—S—CH₃ | —H | t-C₄H₉ | —S-(4-methyl-thiazol-2-yl) |

-continued

| Ex. | R$_4$ | A—Y—R$_2$ | R$_1$ | R | X |
|---|---|---|---|---|---|
| 20 | H$_3$CO—⟨phenyl⟩—CH$_2$— | —CH$_2$—O—CH$_3$ | —OCH$_3$ | —CH$_2$CCl$_3$ | 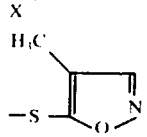 |
| 21 | H$_3$C—⟨phenyl⟩— | —CH$_2$—CH(CH$_3$)—O—CH$_3$ | —H | —CH(⟨phenyl⟩)$_2$ | 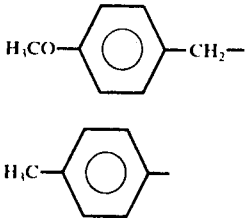 |
| 22 | ⟨thienyl⟩ | —CH(CH$_3$)—CH$_2$—S—CH$_3$ | —OCH$_3$ | —CH(CH$_3$)—O—C(=O)—CH$_3$ | 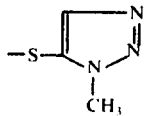 |
| 23 | ⟨phenyl⟩ | —CH$_2$—O—CH$_3$ | —H | Si(CH$_3$)$_3$ |  |
| 24 | ⟨cyclohexyl⟩ | —C(CH$_3$)$_2$—CH$_2$—S—CH$_3$ | —H | —CH$_2$—⟨phenyl⟩ | 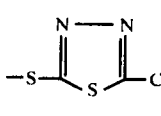 |
| 25 | ⟨cyclopentyl⟩ | —CH$_2$—O—C$_2$H$_5$ | —OCH$_3$ | t-C$_4$H$_9$ | 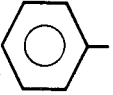 |
| 26 | ⟨cyclohexenyl⟩ | —(CH$_2$)$_2$—O—CH$_3$ | —H | —CH(⟨phenyl⟩)$_2$ | 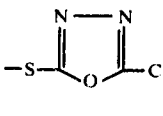 |
| 27 | ⟨cyclohexadienyl⟩ | —CH$_2$—S—CH$_3$ | —H | —CH(⟨phenyl⟩)$_2$ | —H |
| 28 | ⟨cyclohexadienyl⟩ | —CH$_2$—O—CH(CH$_3$)$_2$ | —OCH$_3$ | —CH(⟨phenyl⟩)$_2$ | 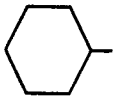 |
| 29 | —C$_2$H$_5$ | —CH$_2$—S—C$_2$H$_5$ | —H | t-C$_4$H$_9$ | 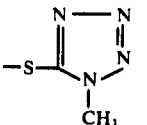 |
| 30 | H— | —CH$_2$—O—CH$_3$ | —H | —CH$_2$CCl$_3$ | —O—C(=O)—CH$_3$ |

The compounds of Col. I may be in the D-, the L-, or the D,L-isomeric form.

EXAMPLE 31

7β-[[D-[[[(Methoxymethyl)methylamino]carbonyl]-amino]-2-thienyl-acetyl]amino]-3-[[(1-methyl-1H-tetrazol-5-yl)thio]methyl]-8-oxo-5-thia-1-azabicyclo[4.2.0]oct-2-ene-2-carboxylic acid 0.291 g. (0.0005 mole) of the trifluoroacetic acid salt product from Example 1(e) are suspended in 4 ml. of acetone, 1 ml. of propylene oxide is added and the mixture is cooled to 0°–5°. After the addition of 0.5 ml. of bis-trimethylsilyl acetamide (BSA) a clear solution of the trimethylsilyl ester of the trifluoroacetic acid salt results. To this solution is added with stirring at 0°–5° a solution of 0.0005 moles of (N-methoxymethyl)N-methylcarbamoyl chloride in 2 ml. of acetone. The solution is allowed to come to room temperature and is stirred for an additional hour. Then 4 ml. of water are added and the pH of the mixture is adjusted to 8.5. This mixture is extracted twice with ethyl acetate. The aqueous phase is then layered over with fresh ethyl acetate and the pH is adjusted to 2. The ethyl acetate layer is then separated, washed with water, dried over magnesium sulfate and concentrated. Upon triturating the residue with petroleum ether, 7β-[[D-[[[(methoxymethyl)methylamino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid is obtained.

An aqueous equimolar solution of this acid and sodium or potassium bicarbonate can be lyophilized to yield the corresponding sodium or potassium salt.

In an analogous manner, the corresponding L-isomer compound can be prepared.

EXAMPLES 32–52

Following the procedure of example 31 but employing the trifluoroacetic acid salt shown in Col. I and the carbamoyl chloride shown in Col. II or the carbamothioic acid, S-phenyl ester shown in Col. III one obtains the final product of Col. IV. The acid of Col. IV can then be treated so as to introduce a salt ion or ester group.

Col. I
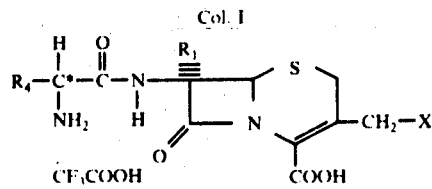

Col. II
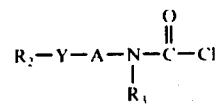

Col. III
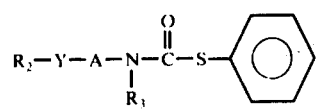

Col. IV
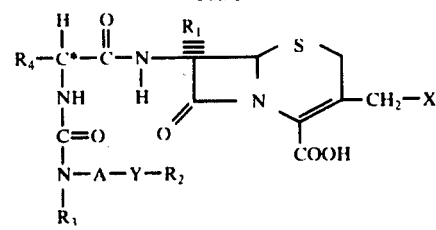

| Ex. | R₄ | A—Y—R₂ | R₃ | R₁ | X |
|---|---|---|---|---|---|
| 32 |  | —CH₂—S—CH₃ | —CH₃ | —H | 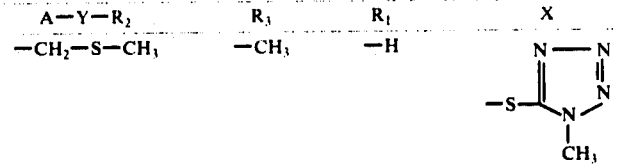 |
| 33 |  | —CH₂—O—CH₃ | —CH₃ | —OCH₃ | 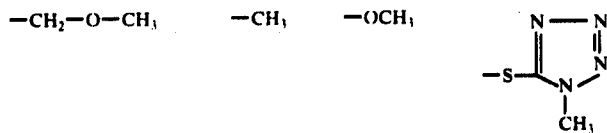 |
| 34 |  | —CH₂—O—CH₃ | —CH₃ | —H | 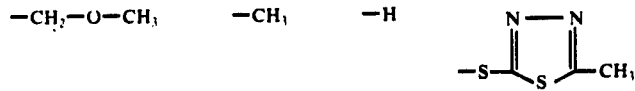 |
| 35 | 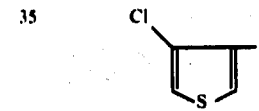 | —CH—S—CH₃<br>\|<br>CH₃ | —CH₃ | —OCH₃ | 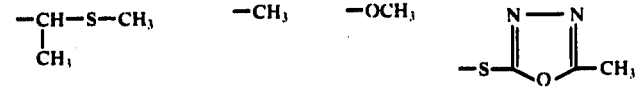 |
| 36 |  | —CH₂—O—C₂H₅ | —C₂H₅ | —H | 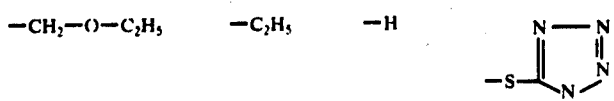 |
| 37 | 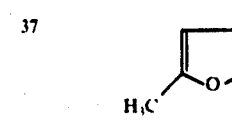 | CH₃<br>\|<br>—C—S—CH₃<br>\|<br>CH₃ | —H | —OCH₃ | 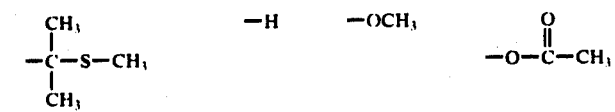 |
| 38 | 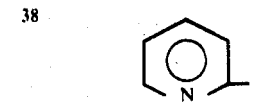 | —(CH)₂—O—C₂H₅ | CH₃<br>\|<br>—CH<br>\|<br>CH₃ | —H | 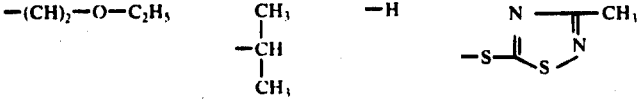 |
| 39 | 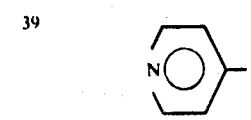 | —(CH₂)₃—S—CH₃ | —CH₃ | —OCH₃ | 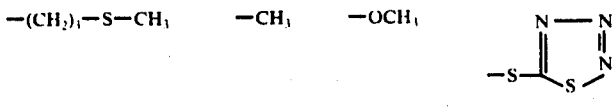 |

-continued

| Ex. | R₄ | A—Y—R₂ | R₃ | R₁ | X |
|---|---|---|---|---|---|
| 40 | phenyl | —CH₂—O—CH₃ | —CH₃ | —H | 1-methyl-tetrazol-5-yl-thio |
| 41 | phenyl | —CH₂—S—CH₃ | —CH₃ | —OCH₃ | 1-methyl-tetrazol-5-yl-thio |
| 42 | 4-hydroxyphenyl | —CH₂—O—CH₃ | —CH₃ | —OCH₃ | 1-methyl-tetrazol-5-yl-thio |
| 43 | 4-hydroxyphenyl | —CH₂—S—CH₃ | —CH₃ | —H | 1-methyl-tetrazol-5-yl-thio |
| 44 | 2,4-dichlorophenyl | —CH₂—O—CH(CH₃)₂ | —CH₃ | —OCH₃ | 1H-1,2,3-triazol-5-yl-thio |
| 45 | 4-methylbenzyl | —CH₂—S—C(CH₃)₃ | —C₂H₅ | —H | 1-methyl-1,2,3-triazol-5-yl-thio |
| 46 | phenethyl | —CH(CH₃)—O—CH₃ | —C(CH₃)₃ | —H | 3-methyl-isothiazol-5-yl-thio |
| 47 | 4-methoxybenzyl | —(CH₂)₄—S—CH₃ | —CH₃ | —OCH₃ | 3-methyl-isoxazol-5-yl-thio |
| 48 | phenyl | —CH₂—O—C₂H₅ | —CH₃ | —H | 5-ethyl-1,3,4-thiadiazol-2-yl-thio |
| 49 | cyclohexa-1,3-dienyl | —CH₂—S—CH₃ | —C₂H₅ | —H | —H |
| 50 | cyclohexa-1,3-dienyl | —CH₂—O—CH₃ | —CH₃ | —OCH₃ | 5-methyl-1,3,4-oxadiazol-2-yl-thio |
| 51 | cyclohexenyl | —CH₂—S—CH₃ | —CH₃ | —H | 1-ethyl-tetrazol-5-yl-thio |

-continued

| Ex. | R$_4$ | A—Y—R$_2$ | R$_3$ | R$_1$ | X |
|---|---|---|---|---|---|
| 52 | C$_2$H$_5$— | —CH$_2$—O—C$_2$H$_5$ | —CH$_3$ | —H | —O—$\overset{\overset{O}{\|\|}}{C}$—C$_2$H$_5$ |

The compounds of Col. I may be in the D-, the L-, or the D,L-isomeric form.

EXAMPLE 53

7β-[[D-[[[(Methoxymethyl)amino]carbonyl]amino]-2-thienylacetyl]-amino]-3-[[4-(aminocarbonyl)pyridino]-methyl]-8-oxo-5-thia-1-azabicyclo[4.2.0]oct-2-ene-2-carboxylic acid a. 3-[(Acetoxy)methyl-7β-[[D-[[[(4-methoxyphenyl)methoxy]-carbonyl]amino]-2-thienylacetyl]amino]-8-oxo-5-thia-1-azabicyclo[4.2.0]oct-2-ene-2-carboxylic acid 3.2 g. (0.01 mole) of the D-2-[[[(4-methoxyphenyl)-methoxy]carbonyl]amino]-2-thiopheneacetic acid from example 1(a) are brought into solution in 40 ml. of methylene chloride with 1.1 ml. of N-methylmorpholine. The solution is cooled to −15°, 1.39 ml. of isobutylchloroformate are added, and the mixture is stirred for 10 minutes. To this is added a solution of 3.26 g. (0.1012 mol.) of 7-aminocephalosporanic acid and 3.1 ml. of triethylamine in 40 ml. of methylene chloride. The mixture is stirred for 1 hour at −5° and 1 hour at 5°. This mixture is then evaporated to dryness in a rotary evaporator. The solid residue is triturated with ether and filtered under suction. The substance is then dissolved in ice water, layered over with ethyl acetate and acidified to pH 2.5. The layers are separated, the aqueous layer is extracted once more with ethyl acetate, the combined ethyl acetate extracts are washed with water, dried with magnesium sulfate and concentrated. The residue (4.9 g.) is dissolved in 200 ml. of ethyl acetate and the solution is treated with activated carbon. After filtration, 2 g. of 3-[(acetyloxy)methyl]-7β-[[D-[[[(4-methoxyphenyl)methoxy]carbonyl]amino]-2-thienyl-acetyl]amino]-8-oxo-5-thia-1-azabicyclo[4.2.0]oct-2-ene-2-carboxylic acid, crystallize; m.p. 142°-143° (dec.).

b. 3-[(Acetyloxy)methoxy]-7β-[D-2-amino-2-(2-thienyl)acetamido]-8-oxo-5-thia-1-azabicyclo[4.2.0]oct-2-ene-2-carboxylic acid, trifluoroacetic acid salt (1:1)

2.0 g. of the product from part (a) are added at −5° to a mixture of 10 ml. of trifluoroacetic acid and 4 ml. of anisole. The mixture is stirred for 10 minutes and is then concentrated in a rotary evaporator. The residue is treated with ether and filtered to yield the titled compound.

c. 3-[(Acetyloxy)methyl]-7β-[[D-[[[(methoxymethyl)amino]-carbonyl]amino]-2-thienylacetyl]amino]-8-oxo-5-thia-1-azabicyclo[4.2.0]oct-2-ene-2-carboxylic acid, sodium salt The trifluoroacetic acid salt product from part (b) and isocyanic acid, methoxymethyl ester are reacted according to the procedure of example 1(f) to yield 3-[(acetyloxy)-methyl]-7β-[[D-[[[(methoxymethyl)amino]carbonyl]amino]-2-thienylacetyl]amino]-8-oxo-5-thia-1-azabicyclo[4.2.0]oct-2-ene-2-carboxylic acid, triethylamine salt. This triethylamine salt is treated as in example 1(g) to yield the free acid and then treated with sodium bicarbonate to yield 3-[(acetyloxy)methyl]-7β-[[D-[[[(methoxymethyl)amino]carbonyl]-amino]-2-thienylacetyl]amino]-8-oxo-5-thia-1-azabicyclo[4.2.0]-oct-2-ene-2-carboxylic acid, sodium salt.

d. 7β-[[D-[[[(Methoxymethyl)amino]carbonyl]amino]-2-thienylacetyl]amino]-3-[[4-(aminocarbonyl)pyridino]-methyl]-8-oxo-5-thia-1-azabicyclo[4.2.0]oct-2-ene-2-carboxylic acid A mixture of 0.005 mole of the sodium salt product of part (c), 0.0075 mole of 4-pyridinecarboxamide, 12 g. of potassium thiocyanate and 7.5 ml. of water are heated at 50° for 24 hours. The clear solution is passed through a chromatography column filled with 150 g. of ion exchanger Amberlite XAD-2. The column is eluted with water and all fractions in which the desired product is shown by thin layer chromatography are combined. The combined fractions are lyophilized. The amorphous residue is triturated with ether and filtered under suction to yield 7β-[[D-[[[(methoxymethyl)amino]carbonyl]amino]-2-thienylacetyl]amino]-3-[[4-(aminocarbonyl)pyridino]methyl]-8-oxo-5-thia-1-azabicyclo[4.2.0]oct-2-ene-2-carboxylic acid.

Similarly, by employing L-2-[[[(4-methoxyphenyl)-methoxy]carbonyl]amino]-2-thiopheneacetic acid in place of the D-isomer in the above procedure, one obtains 7β-[[L-[[[(methoxymethyl)amino]carbonyl]-amino]-2-thienylacetyl]-amino]-3-[[4-(aminocarbonyl)-pyridino]methyl]-8-oxo-5-thia-1-azabicyclo[4.2.0]oct-2-ene-2-carboxylic acid.

EXAMPLES 54–68

Following the procedure of example 53, but employing the cephalosporanic acid sodium salt of Col. I and the pyridine compound of Col. II, one obtains the product shown in Col. III.

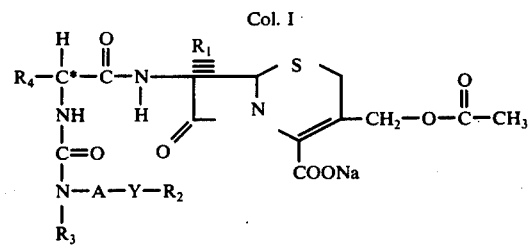

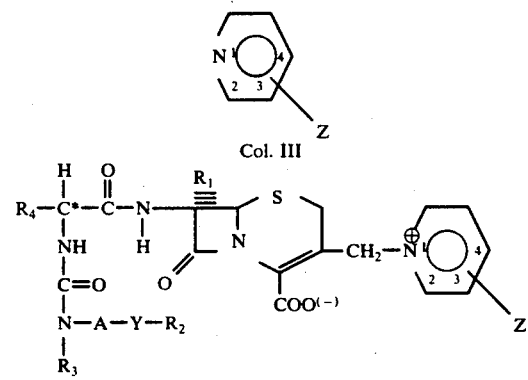

| Ex. | R₄ | R₃ | A—Y—R₂ | R₁ | Z |
|---|---|---|---|---|---|
| 54 | 2-thienyl | —H | —CH₂—S—CH₃ | —OCH₃ | —C(O)—NH₂ (4) |
| 55 | 4-chloro-2-thienyl | —CH₃ | —(CH₂)₂—O—C₂H₅ | —H | —C(O)—NH₂ (4) |
| 56 | 2-thienyl | —C₂H₅ | —CH(CH₃)—CH₂—S—C₂H₅ | —H | —H |
| 57 | 2-furyl | —H | —CH(CH₃)—(CH₂)₂—O—CH₃ | —OCH₃ | —C(O)—NH₂ (4) |
| 58 | 2-furyl | —H | —(CH₂)₄—S—CH₃ | —H | —C(O)—NH₂ (2) |
| 59 | 2-pyridyl | —H | —C(CH₃)₂—CH₂—O—CH₃ | —H | —H |
| 60 | phenyl | —H | —CH₂—O—CH₃ | —H | —C(O)—NH₂ (4) |
| 61 | 4-hydroxyphenyl | —H | —CH₂—S—CH₃ | —OCH₃ | —C(O)—NH₂ (4) |
| 62 | phenyl | —CH₃ | —CH₂—O—C₂H₅ | —OCH₃ | —C(O)—NH₂ (4) |
| 63 | 4-hydroxyphenyl | —CH₃ | —CH(CH₃)—CH₂—S—CH₃ | —OCH₃ | —C(O)—NH₂ (4) |
| 64 | benzyl | —C₂H₅ | —(CH₂)₃—O—CH₃ | —H | —H |
| 65 | 4-methoxyphenyl | —H | —CH₂—S—CH(CH₃)₂ | —OCH₃ | —C(O)—NH₂ (3) |
| 66 | cyclohexyl | —H | —CH₂—CH(CH₃)—CH₂—O—CH₂ | —H | —C(O)—NH₂ (4) |
| 67 | cyclohexenyl | —CH₃ | —CH₂—S—C(CH₃)₃ | —OCH₃ | —H |

| Ex. | R_4 | R_3 | A—Y—R_2 | R_1 | Z |
|---|---|---|---|---|---|
| 68 | (phenyl) | —H | —CH$_2$—O—CH$_3$ | —H | $\overset{O}{\underset{\|}{-C}}$—NH$_2$ (4) |

The sodium salts of Col. I may be in the D-, the L-, or the D,L-isomeric form.

EXAMPLE 69

7β-[[D-[[[(Methoxymethyl)amino]carbonyl]amino]-2-thienylacetyl]amino]-3-[[(1-oxo-2-pyridinyl)thio]methyl]-8-oxo-5-thia-1-azabicyclo[4.2.0]oct-2-ene-2-carboxylic acid 0.003 mole of 3-[(acetyloxy)methyl]-7β-[[D-[[[(methoxymethyl)amino]carbonyl]amino]-2-thienylacetyl]amino]-8-oxo-5-thia-1-azabicyclo[4.2.0]oct-2-ene-2-carboxylic acid, sodium salt from example 53(c) and 0.004 mole of 2-mercaptopyridine, 1-oxide sodium salt are dissolved in 15 ml. of water and heated overnight at 50°. The reaction mixture is then diluted with water, filtered, and the clear solution is adjusted to a pH of 2 by the addition of 2N hydrochlorice acid. The resulting precipitate is filtered under suction to obtain 7β-[[D-[[[(methoxymethyl)amino]-carbonyl]amino]-2-thienylacetyl]amino]-3-[[(1-oxo-2-pyridinyl)-thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(methoxymethyl)amino]-carbonyl]-amino]-2-thienylacetyl]amino]-8-oxo-5-thia-1-azabicyclo-[4.2.0]oct-2-ene-2-carboxylic acid, sodium salt, one obtains the corresponding final product in the L-form.

Similarly, the various 3-[(acetyloxy)methyl]-7α-methoxy or desmethoxy-7β-acylureido-cephalosporanic acid sodium salts of Col. I of examples 54 to 68 may be employed in the procedure of example 69 to obtain other 3-[[(1-oxo-2-pyridinyl)thio]methyl]cephalosporins within the scope of the invention.

EXAMPLE 70

7β-[[D-[[[(Methoxymethyl) amino]carbonyl]amino]-2-thienylacetyl]-amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(methoxymethyl)amino]-carbonyl]amino]-2-thienylacetyl]amino]-8-oxo-5-thia-1-azabiyclo-[4.2.0]oct-2-ene-2-caboxylic acid, sodium salt from example 53(c) is dissolved in a mixture of acetone:,water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[[D-[[[(methoxymethyl)amino]carbonyl]amino]-2-thienylacetyl]-amino]-3-[[(1-oxopyridazin-3-yl)thio]methyl]-8-oxo-5-thia-1-azabicyclo[4.2.0]oct-2-ene-2-carboxylic acid.

Following the same procedure but employing 3-[(acetyloxy)methyl]-7β-[[L-[[[(methoxymethyl) amino]carbonyl]amino]-2-thienylacetyl]amino]-8-oxo-5-thia-1-azabicyclo[4.2.0]oct-2-ene-2-carboxylic acid, sodium salt, one obtains the corresponding final product in the L- form.

EXAMPLES 71-79

Following the procedure of example 70 but substituting for the 1-oxopyridazine-3-thiol one of the following:
2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol
one obtains:
7β-[[D-[[[(methoxymethyl)amino]carbonyl]amino]-2-thienylacetyl]amino]-3-[[(2-oxopyridazin-3-yl)thio]methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-methyl-1-oxopyridazin-3-yl)thio]-methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-methoxy-1-oxopyridazin-3-yl)thio]-methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-t-butyl-2-oxopyridazin-3-yl)thio]-methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-ethyl-2-oxopyridazin-3-yl)thio]-methyl]-8-oxo-5-thia-1-azabicyclo[4.2.0]oct-2-ene-2-carboxylic acid, 7β-[[D-[[[(methoxymethyl amino]carbonyl]amino]-2-thienylacetyl]amino]-3-[[(6-hydroxy-1-oxopyridazin-3-yl)thio]methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-hydroxy-2-oxopyridazin-3-yl)thio]methyl]-8-oxo-5-thia-1-azabicyclo[4.2.0]oct-2-ene-2-carboxylic acid, 7β-[[D-[[[(methoxymethyl)amino]carbonyl]amino]-2-thienylacetyl]amino]-3-[[(6-chloro-1-oxopyridazin-3-yl)thio]methyl]-8-oxo-5-thia-1-azabicyclo[4.2.0]oct-2-ene-2-carboxylic acid, and 7β-[[D-[[[(methoxymethyl)amino]carbonyl]amino]-2-thienylacetyl]amino]-3-[[(6-chloro-2-oxopyridazin-3-yl)thio]methyl]-8-oxo-5-thia-1-azabicyclo[4.2.0]oct-2-ene-2-carboxylic acid, respectively.

Similarly, by employing 3-[(acetyloxy)methyl]-7β-[[L-[[[(methoxymethyl)amino]carbonyl]amino]-2-thienylacetyl]-amino-8-oxo-5-thia-1-azabicyclo[4.2.0]-oct-2-ene-2-carboxylic acid, sodium salt in place of the D-isomer in examples 71 to 79, the corresponding final products in the L-isomer form are obtained. Additionally, the various 3-[(acetyloxy)methyl]-7α-methoxy or desmethoxy-7β-acylureido-cephalosporanic acid sodium salts shown in Col. I of examples 54 to 68 may be employed in the procedure of examples 70 to 79 to obtain other compounds within the scope of the invention.

EXAMPLES 80-90

Following the procedure of example 70 but employing the 3-[(acetyloxy)methyl]-7α-methoxy of desmethoxy-7-acylureido cephalosporin disodium salt of Col. I and the heteromercapto of Col. II, one obtains the 3-heterothio compounds of Col. III.

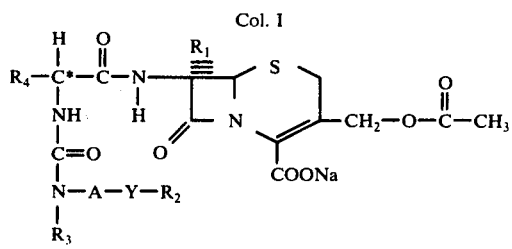

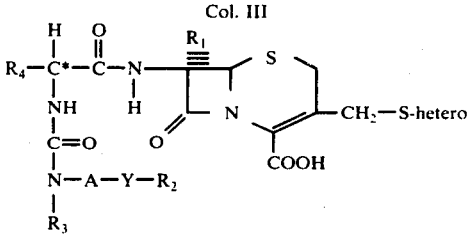

| Ex. | R$_4$ | R$_3$ | A—Y—R$_2$ | R$_1$ | hetero |
|---|---|---|---|---|---|
| 80 | (2-thienyl) | —C$_2$H$_5$ | —CH$_2$—O—CH$_3$ | —OCH$_3$ | 1-methyltetrazol-5-yl |
| 81 | (5-methyl-2-furyl) | —H | —CH(CH$_3$)—CH$_2$—S—CH$_3$ | —H | 5-methyl-1,3,4-thiadiazol-2-yl |
| 82 | (4-pyridyl) | —CH$_3$ | —(CH$_2$)$_3$—O—C$_2$H$_5$ | —H | 5-methyl-1,3,4-thiadiazol-2-yl |
| 83 | (phenyl) | —H | —C(CH$_3$)$_2$—S—C(CH$_3$)$_3$ | —OCH$_3$ | 1-methyltetrazol-5-yl |
| 84 | (4-chlorobenzyl) | t-C$_4$H$_9$ | —(CH$_2$)$_2$—O—CH$_3$ | —H | 1H-1,2,3-triazol-4-yl |
| 85 | (4-hydroxyphenyl) | —C$_2$H$_5$ | —CH$_2$—S—C$_2$H$_5$ | —OCH$_3$ | 1,3,4-thiadiazol-2-yl |
| 86 | (2-phenylethyl) | —H | —(CH$_2$)$_4$—O—CH$_3$ | —H | 4-methylthiazol-2-yl |
| 87 | (cyclohexenyl) | —CH$_3$ | —CH(C$_2$H$_5$)—CH$_2$—O—CH$_2$ | —OCH$_3$ | 3-ethylisoxazol-5-yl |
| 88 | (cyclohexenyl) | —H | —CH(CH$_3$)—CH$_2$—O—C$_2$H$_5$ | —H | 1-ethyltetrazol-5-yl |

| Ex. | R₄ | R₃ | A—Y—R₂ | R₁ | hetero |
|---|---|---|---|---|---|
| 89 | 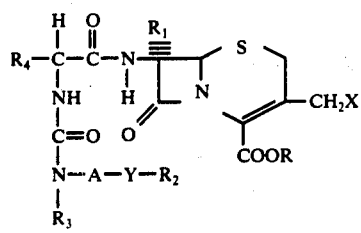 | —H | —CH₂—S—C₂H₅ | —H | 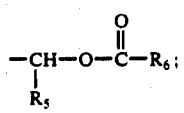 |
| 90 | C₂H₅— | —H | —CH₂—O—CH₃ | —OCH₃ | |

The sodium salt compounds of Col. I can be in the D-, the L-, or the D,L-isomeric form.

What is claimed is:

1. A compound of the formula

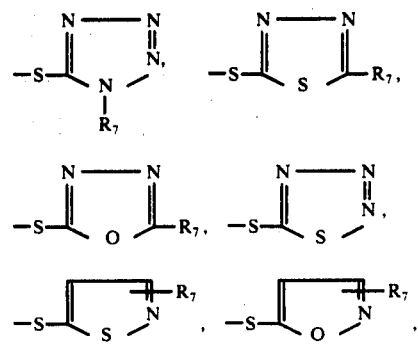

wherein R is hydrogen, lower alkyl, phenyl-lower alkyl, diphenyl-lower alkyl, tri(lower alkyl)silyl, trihaloethyl, an alkali metal ion, an alkaline earth metal ion, dibenzylamine, N,N-dibenzylethylenediamine, methylamine, triethylamine, N-ethylpiperidine, or $$-\text{CH}-\text{O}-\overset{\text{O}}{\overset{\|}{\text{C}}}-\text{R}_6;$$
$$\overset{|}{\text{R}_5}$$

R₁ is in the α-configuration and is hydrogen or methoxy; R₂ is lower alkyl; Y is O or S; R₃ is hydrogen or lower alkyl; A is straight or branched chain alkylene of 1 to 6 carbons; R₄ is phenyl, phenyl-lower alkyl, substituted phenyl or phenyl-lower alkyl wherein said phenyl substituent is one or two members selected from the group consisting of halogen, lower alkyl of 1 to 4 carbons, lower alkoxy of 1 to 4 carbons, and hydroxy, or a substituted or unsubstituted heterocyclic selected from the group consisting of 2-thienyl, 3-thienyl, 2-furyl, and 3-furyl wherein said heterocyclic substituent is attached at an available carbon atom and is halogen or lower alkyl of 1 to 4 carbons; R₅ is hydrogen or lower alkyl; R₆ is lower alkyl; and X is a heterothio selected from the group consisting of

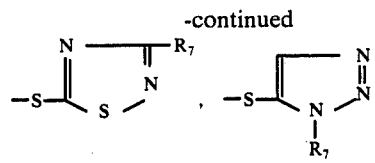

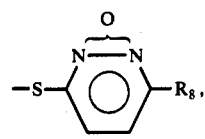

and

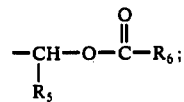

wherein R₇ is hydrogen or lower alkyl of 1 to 4 carbons and R₈ is hydrogen, lower alkyl of 1 to 4 carbons, methoxy, hydroxy, or halogen.

2. The compound of claim 1 wherein R is hydrogen, straight or branched chain alkyl of 1 to 4 carbons, benzyl, phenethyl, diphenylmethyl, trimethylsilyl, 2,2,2-trichloroethyl, an alkali metal ion, an alkaline earth metal ion, dibenzylamine, N,N-dibenzylethylenediamine, methylamine, triethylamine, N-ethylpiperidine, or $$-\text{CH}-\text{O}-\overset{\text{O}}{\overset{\|}{\text{C}}}-\text{R}_6;$$
$$\overset{|}{\text{R}_5}$$

R₂ is lower alkyl of 1 to 4 carbons; Y is O or S; R₃ is hydrogen or lower alkyl of 1 to 4 carbons; A is straight or branched chain alkylene of 1 to 4 carbons; R₄ is phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a substituted or unsubstituted heterocyclic selected from the group consisting of 2-thienyl, 3-thienyl, 2-furyl, and 3-furyl wherein said heterocyclic substituent is attached at an available carbon atom and is chloro, bromo, methyl, or ethyl; R₅ is hydrogen or straight or branched chain alkyl of 1 to 4 carbons; R₆ is straight or branched chain alkyl of 1 to 4 carbons; and X is a heterothio selected from the group consisting of

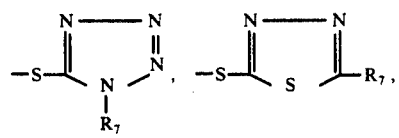

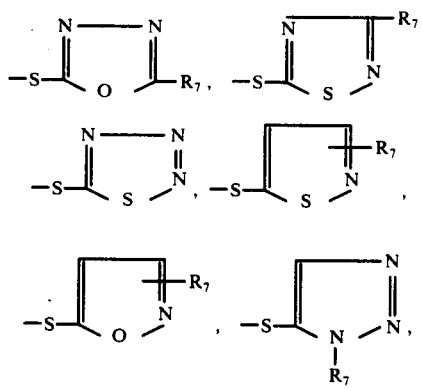

and

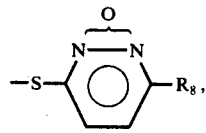

wherein R₇ is hydrogen, methyl or ethyl and R₈ is hydrogen, methyl, ethyl, methoxy, hydroxy, or chlorine.

3. The compound of claim 2 wherein R is hydrogen, triethylamine, sodium or potassium; R₄ is 2-thienyl, 3-thienyl, phenyl, or 4-hydroxyphenyl; and R₃ is hydrogen.

4. The compound of claim 3 wherein X is

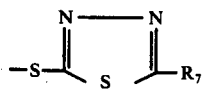

and R₇ is hydrogen, methyl, or ethyl.

5. The compound of claim 3 wherein X is

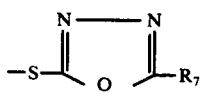

and R₇ is hydrogen, methyl, or ethyl.

6. The compound of claim 3 wherein X is

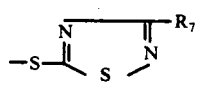

and R₇ is hydrogen, methyl, or ethyl.

7. The compound of claim 3 wherein X is

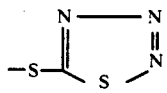

8. The compound of claim 3 wherein X is

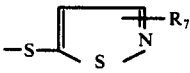

and R₇ is hydrogen, methyl, or ethyl.

9. The compound of claim 3 wherein X is

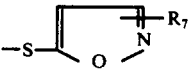

and R₇ is hydrogen, methyl, or ethyl.

10. The compound of claim 3 wherein X is

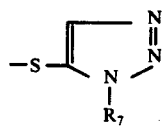

and R₇ is hydrogen, methyl, or ethyl.

11. The compound of claim 3 wherein X is

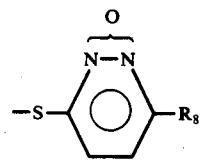

and R₈ is hydrogen, methyl, ethyl, methoxy, hydroxy, or chlorine.

12. The compound of claim 3 wherein X is

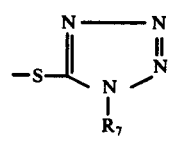

and R₇ is hydrogen, methyl, or ethyl.

13. The compound of claim 12 wherein R₇ is methyl.

14. The compound of claim 13 wherein R₁ is methoxy and R₄ is 2-thienyl.

15. The compound of claim 13 wherein R₁ is hydrogen and R₄ is 2-thienyl.

16. The compound of claim 15 wherein Y is O; R is triethylamine; and R₂ is —CH₃.

17. The compound of claim 15 wherein Y is O; R is hydrogen; and R₂ is —CH₃.

18. The compound of claim 15 wherein Y is O; R is sodium; and R₂ is —CH₃.

* * * * *

UNITED STATES PATENT OFFICE
CERTIFICATE OF CORRECTION

Patent No. 4,049,651     Dated September 20, 1977

Inventor(s) Hermann Breuer, et al.

It is certified that error appears in the above-identified patent and that said Letters Patent are hereby corrected as shown below:

Column 5, line 6, "of th formula" should read --of the formula--.

Column 6, line 18, "halo-R—(XII)" should read
-- halo-R                                          (XIII) --.

Column 8, line 25, "to warn to" should read --to warm to--.

Column 9, line 18, "treatd with" should read --treated with--.

Column 9, line 33, "(d) are addd" should read --(d) are added--.

Column 10, line 42, "an also" should read --and also--.

Column 21, line 55, ")amino]-carbonyl]" should read
-- )amino]carbonyl] --.

Signed and Sealed this

Twenty-fifth Day of April 1978

[SEAL]

Attest:

RUTH C. MASON        LUTRELLE F. PARKER
Attesting Officer        Acting Commissioner of Patents and Trademarks